US012746236B2

(12) United States Patent
Cohen et al.

(10) Patent No.: US 12,746,236 B2
(45) Date of Patent: Sep. 29, 2026

(54) QUININE AND ITS USE TO GENERATE INNATE IMMUNE RESPONSE

(71) Applicant: The Trustees of the University of Pennsylvania, Philadelphia, PA (US)

(72) Inventors: Noam Cohen, Bala Cynwyd, PA (US); Robert J. Lee, Philadelphia, PA (US); Susan R. Weiss, Merion, PA (US); Joel N. Maslow, Devon, PA (US); Christine C. Roberts, Zionsville, PA (US); Sara Cherry, Philadelphia, PA (US); Michael Kohanski, Penn Valley, PA (US); Nithin D. Adappa, Philadelphia, PA (US); James N. Palmer, Penn Valley, PA (US); Li Hui Tan, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 863 days.

(21) Appl. No.: 17/996,853

(22) PCT Filed: Apr. 21, 2021

(86) PCT No.: PCT/US2021/028463
§ 371 (c)(1),
(2) Date: Oct. 21, 2022

(87) PCT Pub. No.: WO2021/216759
PCT Pub. Date: Oct. 28, 2021

(65) Prior Publication Data

US 2023/0144186 A1 May 11, 2023

Related U.S. Application Data

(60) Provisional application No. 63/013,438, filed on Apr. 21, 2020.

(51) Int. Cl.
*A61K 31/49* (2006.01)
*A61K 9/00* (2006.01)
*A61P 31/14* (2006.01)
*G01N 33/569* (2006.01)

(52) U.S. Cl.
CPC ........... *A61K 31/49* (2013.01); *A61K 9/0043* (2013.01); *A61P 31/14* (2018.01); *G01N 33/56983* (2013.01); *G01N 2333/165* (2013.01)

(58) Field of Classification Search
CPC ....... A61K 31/49; A61K 9/0043; A61P 31/14; A61P 11/00; G01N 33/56983; G01N 2333/165; Y02A 50/30
See application file for complete search history.

(56) References Cited

U.S. PATENT DOCUMENTS

| | | | | |
|---|---|---|---|---|
| 10,881,698 B2 * | 1/2021 | Cohen | .................. | A61K 31/167 |
| 2004/0053858 A1 * | 3/2004 | Berg | ...................... | A61K 31/35 514/456 |
| 2004/0167162 A1 | 8/2004 | Charous | | |
| 2015/0017099 A1 | 1/2015 | Cohen | | |
| 2016/0199407 A1 | 7/2016 | Banfi | | |
| 2021/0260144 A1 | 8/2021 | Cohen | | |
| 2023/0144186 A1 | 5/2023 | Cohen | | |

FOREIGN PATENT DOCUMENTS

| | | | |
|---|---|---|---|
| JP | 2005512998 | 5/2005 | |
| WO | 2003039546 | 5/2003 | |
| WO | WO-2007052242 A1 * | 5/2007 | ......... C07K 16/1018 |
| WO | 2013112865 | 8/2013 | |
| WO | 2021195765 | 10/2021 | |

OTHER PUBLICATIONS

Duan et al.; Current and Future Therapeutical Approaches for COVID-19); Drug Discovery Today; vol. 25, No. 8; pp. 1545-1552. Published Aug. 2020.*

Wang et al., 2018, "Research Progress of Physiological Functions of G Protein-coupled Bitter Taste Receptors", World Latest Medicne Information (Electronic Version), 18:28-29.

Cohen, Noam A., "The genetics of the bitter taste receptor T2R38 in upper airway innate immunity and implications for chronic rhinosinusitis", The Laryngoscope, vol. 127 (Jan. 2017), pp. 44-51.

Freund, Jenna R. et al., "Activation of airway epithelial bitter taste receptors by Pseudomonas aeruginosa quinolones modulates calcium, cyclic-AMP, and nitric oxide signaling", Journal of Biological Chemistry, vol. 293, No. 25 (May 10, 2018), pp. 9824-9840.

Lee, Robert J. et al., 2012, "T2R38 taste receptor polymorphisms underlie susceptibility to upper respiratory infection", The Journal of clinical investigation 122 (11), 4145-4159.

Lee, Robert J. et al., "Bitter and sweet taste receptors regulate human upper respiratory innate immunity", The Journal of Clinical Investigation, vol. 124, No. 3 (Mar. 2014), pp. 1393-1405.

Li, Xiangqi et al., "Existing bitter medicines for fighting 2019-nCoV-associated infectious diseases", The FASEB Journal, vol. 34, No. 5 (Apr. 13, 2020), pp. 6008-6016.

(Continued)

*Primary Examiner* — Jeffrey T. Palenik

(74) *Attorney, Agent, or Firm* — Riverside Law LLP

(57) ABSTRACT

The invention provides methods and compositions for assaying infectivity of viruses and potential treatments of such viruses in the upper respiratory tract using an air-liquid interface model with nasal epithelium cells; and treatment of viral infections of the upper respiratory tract by treating with bitter taste receptor agonists that stimulate NO production and/or antimicrobial protein production.

13 Claims, 5 Drawing Sheets

(56) References Cited

OTHER PUBLICATIONS

Mischel Fiona: "What You Should Know About Drinks and Foods That Contain Quinine I Livestrong.com", Livestrong. com, Mar. 30, 2020 (Mar. 30, 2020), pp. 1-14, XP055819973, Retrieved from the Internet: URL:https://www.livestrong.com/article/304030-list-of-foods-that-contain-quinine/ [retrieved on Jun. 30, 2021].

* cited by examiner

FIG. 4A
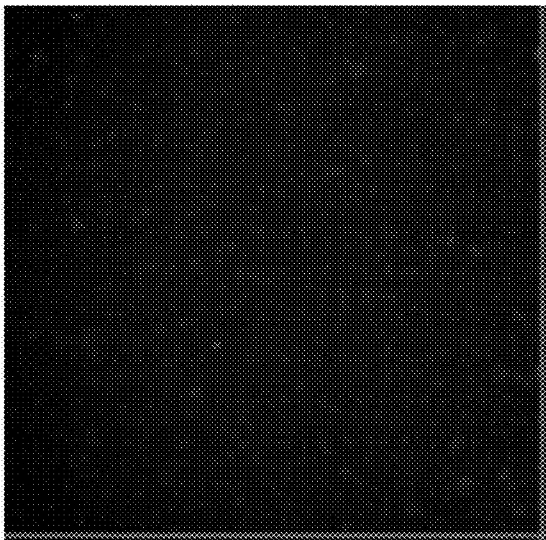
FIG. 4B
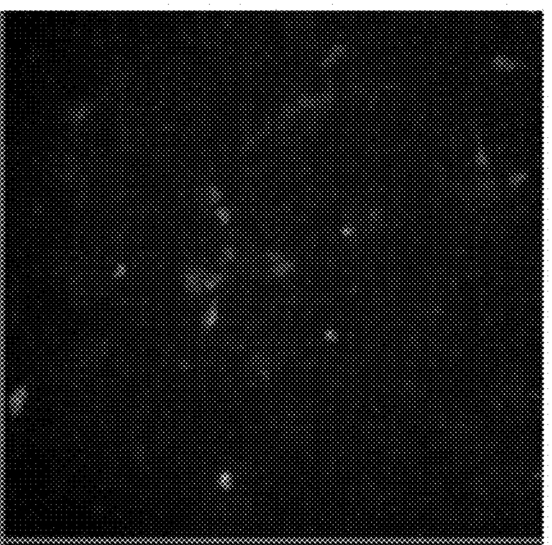
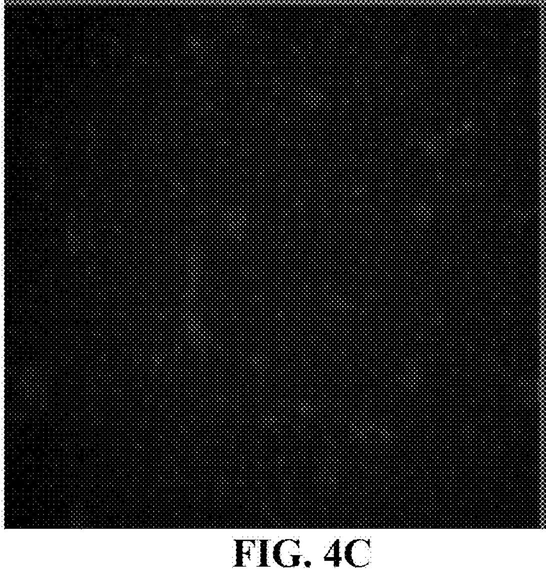
FIG. 4C
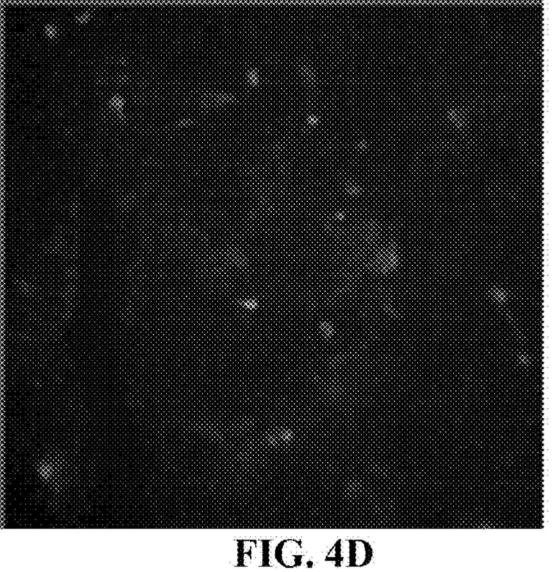
FIG. 4D

QUININE AND ITS USE TO GENERATE INNATE IMMUNE RESPONSE

TECHNICAL FIELD

The invention relates generally to methods and compositions for the treatment of viral infections in the respiratory tract.

BACKGROUND

Viral upper respiratory infections are the most common illnesses for children and adults. These include multiple strains of influenza A such as the H5N1 avian influenza, H1N1 and H3N2 "swine" influenza, influenza B, parainfluenza virus, human metapneumonvirus, rhinovirus, adenovirus, respiratory syncytial virus, and coronaviruses. Children typically experience 7-8 such infections yearly while adults will have 3-4 viral infections each year. Such infections cause significant loss of revenue due to illness in the adult or the needs of increased time spent at home with an ill child. Some of these viruses are associated with significant morbidity and mortality. For example, influenza A virus outbreaks due to H5N1, H7N9, H1N1, and H3N2v had mortality in the 0.5-1.5% range. And adenovirus infection, a cause of conjunctivitis in children and adults, can cause fatal infection in immunosuppressed persons. In addition to coronavirus microbes that are responsible for self-limited upper respiratory infections causing the common cold, three highly pathogenic coronavirus strains have emerged since 2002: the Severe Acute Respiratory Syndrome coronavirus (SARS-CoV), the Middle East Respiratory Syndrome coronavirus (MERS-CoV), and SARS-CoV-2 also referred to COVID-19.

The microbe virus SARS-CoV-2 is causing a currently ongoing pandemic with greater than 2 million confirmed cases worldwide and almost 150,000 deaths. The mortality rate for SARS-CoV-2 has a wide range from 2% in Korea to greater than 10% in other countries. MERS-CoV has been ongoing since 2012 with approximately 3,000 cases worldwide but with a much higher mortality rate of 36%. SARS-CoV emerged in 2002 and over the next year almost 10,000 cases were identified with a mortality rate of approximately 10%. Currently, there is no treatment for SARS-CoV-2, although at least one drug, remdesivir, a nucleoside analog that blocks viral replication may have clinical activity. Similarly, there are no vaccines against SARS-CoV-2.

Quinine is a natural compound that is isolated from the bark of the cinchona tree and has been a treatment for malaria for greater than 200 years. Quinine use was made popular by the British as the main ingredient in tonic water and bitter lemon drink mixers that were similarly used as a means of prophylaxis against malaria in tropical regions. Quinine is a bitter compound that can bind to the bitter taste receptors TAS2R4, TAS2R7, TAS2R10, TAS2R14, TAS2R31, TAS2R39, TAS2R40, TAS2R43. Bitter taste receptors are present on type II taste cells and also are expressed on ciliated nasal epithelial cells and other cells of the respiratory system, gastrointestinal tract, and elsewhere where they have a role in innate immune function (Lee et al., JCI 2012, 2014). Quinine was also shown in a murine model, to reduce airway inflammation (by BAL, histology (decrease in inflammatory infiltrate and airway thickening) and by maintenance of normal PFTs. In the patent publication US 2015/0017099A1, quinine was suggested to have antimicrobial effects by triggering bitter taste receptor signaling pathway, as a part of the innate immunity system.

As the pandemic and concerns with SARS-CoV-2 grows and no treatment exists, there remains a need for effective treatments. Further, there is a need for safe antiviral therapies to treat viral infections in the upper respiratory tract.

SUMMARY

An aspect of the present invention are methods of treating a viral infection in a subject having an upper respiratory infection, comprising dispersing as particulate a formulation of a bitter taste receptor agonist; applying the dispersed formulation onto the mucosal surface of an upper respiratory cavity of the subject; and generating NO production or stimulating antimicrobial peptide production, or both, through the stimulation of bitter taste receptors. The bitter taste receptor agonist is an agonist that causes bitter taste receptor signaling resulting in NO production or stimulating antimicrobial peptide production, or a combination thereof.

In another aspect of the present invention, there are methods of detecting viral infection of nasal epithelium using an air-liquid interface, comprising: establishing a cell culture of human sinonasal epithelial cells grown to confluence in culture flask; differentiating the sinonasal epithelial cells; infecting the epithelial cells on the apical surface with a virus strain known to infect upper respiratory tract of a mammal; treating the sinonasal epithelial cells with a bitter taste receptor agonist; incubating the sinonasal epithelia cells; and analyzing level of viruses released by the sinonasal epithelial cell culture.

In some embodiments, the bitter taste receptor agonist is selected from the group consisting of: denatonium, phenylthiocarbamide (PTC), a homoserine lactone, sodium thiocyanate (NaSCN), 6-n-propylthio uracil (PROP or PTU), parthenolide, amarogentin, antidesma (including its extracts), colchicine, dapsone, salicin, chrysin, apigenin, quinine, and quinine salts. Preferable the agonist is denatonium, absinthin, or quinine and its salts. The viral infection can be an infection resulting from a virus selected from: SARS; SARS-CoV-2; MERS-CoV; SARS-CoV; influenza A, influenza B; parainfluenza virus; rhinovirus; adenovirus; human metapneumovirus; respiratory syncytial virus; and non-pathogenic coronaviruses. Preferably, the dispersing and applying steps are repeated three times per day using a nasal delivery device. The nasal delivery device can be selected from one of a number of available delivery devices that apply formulation to the mucosal layer and can include metered dose inhaler, dry powder inhaler, dropper, nebulizer, atomizer, or lavage.

BRIEF DESCRIPTION OF THE DRAWINGS

FIGS. 4A, 4B, 4C, and 4D depict human sinonasal ALIs infected with the SARS-CoV2 (COVID-19) with staining for the SARS-CoV2 nucleocapsid protein (N) shown in green, as described in the Examples.

DETAILED DESCRIPTION OF EMBODIMENTS

Definitions

Figure 1A:
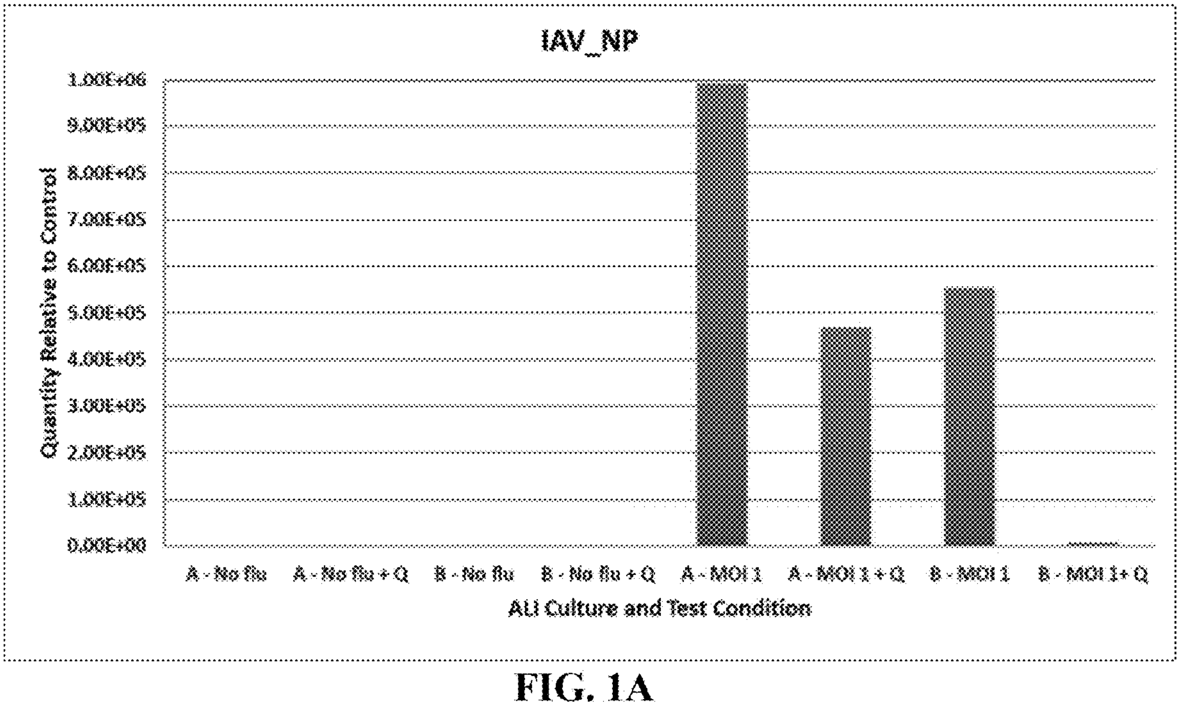
FIGS. 1A and 1B depict the reduction in IAV_NP and IAV_M1 genes when treated with a 0.1% solution of quinine in 0.9% sodium chloride, as described in the Examples.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Immune response" as used herein means the activation of a host's immune system, e.g., that of a mammal, in response to the introduction of antigen. The immune response can be in the form of a cellular or humoral response, or both.

"Innate immunity" as used herein means the nonspecific part of a subject's immune system. Innate immune responses are not specific to a particular pathogen in the way that the adaptive immune responses are. They depend on a group of proteins and phagocytic cells that recognize conserved features of pathogens and become quickly activated to help destroy invaders.

"Subject" as used herein can mean a mammal that is capable of being administered the immunogenic compositions described herein. The mammal can be, for example, a human, chimpanzee, dog, cat, horse, cow, rabbit, groundhog, squirrel, mouse, rat, or other rodents.

"Treatment" or "treating," as used herein can mean protecting of a subject from a disease through means of preventing, suppressing, repressing, or completely eliminating the disease.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Description

In a first aspect, the present invention is directed to methods of treating viral infections of the respiratory tract, especially the upper respiratory tract, using a composition of bitter taste receptor agonist capable of upregulating NO production and/or anti-microbial peptides, which agonists are preferably quinine or a salt thereof, and more preferably quinine sulfate salt. The described methods include topical delivery of the bitter taste receptor agonist quinine administered intranasally via a dispersing device (liquid or solid form) to generate a dispersed form of the composition in the ear-nose-throat tract (or upper respiratory tract) thereby providing prophylaxis and/or treatment against upper respiratory viruses, including SARS; SARS-CoV-2; MERS-CoV; SARS-CoV; influenza virus, which includes multiple strains of influenza A such as the H5N1 avian influenza, H1N1 and H3N2 "swine" influenza, and influenza B; parainfluenza virus; rhinovirus; adenovirus; human metapneumovirus; respiratory syncytial virus, and non-pathogenic coronaviruses.

Bitter taste signaling serves the function of indicating the presence of bacteria in the upper respiratory tract and activating an innate immune response during times of bacterial infection, in addition to the function of detecting the taste of material entered the mouth or nose. The first response to a bitter taste is a signal causing elevation of [Ca2+] in the epithelial cells of the upper respiratory tract. When a bitter taste receptor is activated with a bitter receptor agonist, the intracellular calcium concentration [Ca2+] is elevated, which may also lead to an increased ciliary beat frequency (CBF).

The second response caused by bitter taste signaling activation in epithelial cells, in addition to [Ca2+] elevation, is secretion of antiviral products, which is part of an innate immune reaction. The antiviral products include many peptides, including lysozyme, lactoferrin and defensins, that exhibit activity in suppression or killing of viruses.

Yet another effect of bitter taste signaling activation is nitric oxide (NO) production. Bitter taste receptor agonists capable of activating NO production are preferred for activating an innate immune response against an upper respiratory viral infection. In one example of such bitter taste receptor agonist is quinine, including the salts thereof.

Therefore, interference with certain components of the taste signaling pathways, i.e. activating bitter taste signaling and/or anti-microbial peptide production can be used to activate an immediate and vigorous innate antiviral response in the upper respiratory tract against viral infections. Any components that activate bitter taste signaling to enhance NO production and/or anti-microbial peptide production and thereby enhance the innate antiviral response may be employed in the present invention.

Activation of NO production through and/or anti-microbial peptide production via the bitter taste signaling is preferably accomplished by activating a plurality of bitter taste receptors. There are twenty-five known bitter taste receptors that belong to the T2R family. Different bitter taste receptors may have different affinities for the same agonist. Therefore, the use of bitter taste receptor agonists to activate bitter taste signaling will have varying degrees of activity depending upon which bitter taste receptors the agonist may bind to.

In a preferred embodiment, the bitter taste receptor agonist capable of activating production of NO and/or stimulating production of antimicrobial proteins includes denatonium, phenylthiocarbamide (PTC), a homoserine lactone, sodium thiocyanate (NaSCN), 6-n-propylthio uracil (PROP or PTU), parthenolide, amarogentin, antidesma (including its extracts), colchicine, dapsone, salicin, chrysin, apigenin, quinine, and quinine salts.

In some embodiments, quinine that stimulates nitric oxide (NO) production in sinonasal epithelial cells can be used an agent to activate the bitter taste signal pathway. While in some embodiments, a bitter taste receptor agonist that stimulates anti-microbial peptide production in sinonasal epithelial cells can be used as an agent to activate the bitter taste signal pathway. In other embodiments, an extract or a compound from *Anti desma* sp. (e.g., *Antidesma bunius*) fruits or other parts can be used an agent to activate the bitter taste signal pathway. The extract or compound from *Antidesma* sp. may stimulate NO production in sinonasal epithelial cells includes quinine or salts thereof. Quinine is a basic amine and is usually provided as a salt, which include the hydrochloride, dihydrochloride, sulfate, bisulfate and gluconate salts, and preferably sulfate salt.

In a preferred embodiment, the bitter taste receptor agonist is capable of stimulating antimicrobial peptide production through the bitter taste signaling pathway, which includes denatonium and absinthin. The anti-viral product stimulated by denatonium is at least proteinaceous. Another stimulated antimicrobial peptide is beta-defensin 2, which is induced with denatonium and/or absinthin. Interference with certain components of the taste signaling pathways, i.e. activating bitter taste signaling, can be used to activate an immediate and vigorous innate anti-viral response in the upper respiratory tract. Any components that activate bitter taste signaling and thereby enhancing the innate anti-viral response may be employed in the present invention.

Pharmaceutical Compositions

The compositions of the invention are preferably formulated with a pharmaceutically acceptable carrier. Preferred compositions are compositions that are dispersible so that the bitter taste receptor agonists can be delivered to the mucosal layer in the ENT tract, preferably the upper respiratory tract, and preferably to mucosal layer adjacent to bitter taste receptors.

The compositions provided herein can be applied by direct or indirect means. Direct means include nasal sprays, nasal drops, nasal ointments, nasal washes, nasal lavage, nasal packing, bronchial sprays and inhalers, or any combination of these and similar methods of application. Indirect means include use of throat lozenges, mouthwashes or gargles, or use of ointments applied to the nasal nares, the bridge of the nose, or any combination of these and similar methods of application.

Depending on the desired method of application, the composition may have different viscosity requirements. In one embodiment, the composition has a viscosity sufficiently high to ensure that the composition may adhere to the mucosa for a sufficient time to induce the NO mediated innate immunity against viruses and/or stimulating antimicrobial peptide production. In other words, once the composition is applied to the mucosa of the ENT tract, the composition does not easily flow in the tract due to the relatively high viscosity and/or increases the residence time of the composition on the desired mucosa.

In other embodiments, it may be desirable for the composition to have a relatively low viscosity. For example, when the desired method of application is nasal lavage, the composition is typically applied to the nasal cavity in relatively large quantity. The lavage has two functions: one is washing out the mucus and glucose from the upper respiratory tract, and another is providing an active ingredient to induce the antiviral activity. Thus, to accomplish both functions of a nasal lavage, it may be desirable to have a relatively low viscosity formulation. One preferred embodiment uses a bitter agonist (denatonium or absinthin)-eluting sinus stent as a semi-rigid formulation to stimulate antimicrobial peptide production.

In an exemplary embodiment, the composition may be atomized and sprayed onto the mucosa of the ENT tract, and preferably, the upper respiratory tract. Atomization allows the fine liquid droplets to reach deep into the sinus and other parts of the ENT tract.

The innate antiviral activity is sensitive to salt, presumably because the anti-viral peptides such as lysozyme, lactoferrin, cathelicidin, and beta-defensins are tonically secreted into the respiratory tract. As a result, the antiviral activity of these peptides may be sensitive to ionic strength (which accounts for charge). The composition of present invention is preferably formulated with low strength of ions. The ionic strength may be up to about ~306 mEq/L, the same ionic strength as found in interstitial fluid. The preferred ionic strength is around 50% of PBS (about 150 mEq/L of ions). The preferred range of ionic strength is about 150-200 mEq/L.

The ionic strength in the formulation may vary with the delivery system. A higher volume delivery system (Netti Pot) would allow for a solution closer to the optimal ionic strength range (150-200 mEq/L) because the effects of mixing with mucus would be minimal. A lower volume delivery system may require an even lower ionic strength in the therapeutic solution. In one embodiment, the composition is formulated so that the final ionic strength after the application to the upper respiratory tract is preferably within the range of 150-200 mEq/L.

In general, the composition of the present invention can be in the form of a liquid and/or aerosol including, without limitation, solutions, suspensions, partial liquids, liquid suspensions, sprays, nebulae, mists, atomized vapors and tinctures. In other embodiments, the composition can be in the form of dry powder capable of being dispersed in particulate onto the mucosa of the ENT tract.

In the nasal cavity delivered embodiments, aqueous solutions and suspensions can have dosing volume ranges of 10 μl-2500 μl, 20 μl-2500 μl, 30 μl-2500 μl, 40 μl-2500 μl, 50 μl-2500 μl, 60 μl-2500 μl, 70 μl-2500 μl, 80 μl-2500 μl, 90 μl-2500 μl, 100 μl-2500 μl, 110 μl-2500 μl, 120 μl-2500 μl, 130 μl-2500 μl, 140 μl-2500 μl, 150 μl-2500 μl, 10 μl-2000 μl, 20 μl-2000 μl, 30 μl-2000 μl, 40 μl-2000 μl, 50 μl-2000 μl, 60 μl-2000 μl, 70 μl-2000 μl, 80 μl-2000 μl, 90 μl-2000 μl, 100 μl-2000 μl, 110 μl-2000 μl, 120 μl-2000 μl, 130 μl-2000 μl, 140 μl-2000 μl, 150 μl-2000 μl, 10 μl-1500 μl, 20 μl-1500 μl, 30 μl-1500 μl, 40 μl-1500 μl, 50 μl-1500 μl, 60 μl-1500 μl, 70 μl-1500 μl, 80 μl-1500 μl, 90 μl-1500 μl, 100 μl-1500 μl, 110 μl-1500 μl, 120 μl-1500 μl, 130 μl-1500 μl, 140 μl-1500 μl, 150 μl-1500 μl, 10 μl-1000 μl, 20 μl-1000p, 30 μl-1000 μl, 40 μl-1000 μl, 50 μl-1000 μl, 60 μl-1000 μl, 70 μl-1000 μl, 80 μl-1000p, 90 μl-1000 μl, 100 μl-1000 μl, 110 μl-1000 μl, 120 μl-1000 μl, 130 μl-1000 μl, 140 μl-1000 μl, 150 μl-1000 μl, 10 μl-500 μl, 20 μl-500 μl, 30 μl-500 μl, 40 μl-500 μl, 50 μl-500 μl, 60 μl-500 μl, 70 μl-500 μl, 80 μl-500 μl, 90 μl-500 μl, 100 μl-500 μl, 110 μl-500 μl, 120 μl-500 μl, 130 μl-500 μl, 140 μl-500 μl, 150 μl-500 μl, 10 μl-250 μl, 20 μl-250 μl, 30 μl-250 μl, 40 μl-250 μl, 50 μl-250 μl, 60 μl-250 μl, 70 μl-250 μl, 80 μl-250 μl, 90 μl-250 μl, 100 μl-250 μl, 110 μl-250 μl, 120 μl-250 μl, 130 μl-250 μl, 140 μl-250 μl, 150 μl-250 μl, 10 μl-200 μl, 20 μl-200 μl, 30 μl-200 μl, 40 μl-200 μl, 50 μl-200 μl, 60 μl-200 μl, 70 μl-200 μl, 80 μl-200 μl, 90 μl-200 μl, 100 μl-200 μl, 110 μl-200 μl, 120 μl-200 μl, 130 μl-200 μl, 140 μl-200 μl, 150 μl-200 μl, 10 μl-180 μl, 20 μl-180 μl, 30 μl-180 μl, 40 μl-180 μl, 50 μl-180 μl, 60 μl-180 μl, 70 μl-180 μl, 80 μl-180 μl, 90 μl-180p, 100 μl-180 μl, 110 μl-180 μl, 120 μl-180 μl, 130

µl-180 µl, 140 µl-180 µl, 150 µl-180 µl, 10 µl-160 µl, 20 µl-160 µl, 30 µl-160 µl, 40 µl-160 µl, 50 µl-160 µl, 60 µl-160 µl, 70 µl-160 µl, 80 µl-160 µl, 90 µl-160 µl, 100 µl-160 µl, 110 µl-160 µl, 120 µl-160 µl, 130 µl-160 µl, 140 µl-200 µl, 10 µl-140 µl, 20 µl-140 µl, 30 µl-140 µl, 40 µl-140 µl, 50 µl-140 µl, 60 µl-140 µl, 70 µl-140 µl, 80 µl-140 µl, 90 µl-140 µl, 100 µl-180p, and preferably 50 µl-140 µl and for solution or suspension in pressurized metered dose inhalers (pMDIs). The delivery volumes can be in the range of 10 µl-10,000 µl, 25 µl-9,000 µl, 50 µl-8,000 µl, 100 µl-7,000 µl, 100 µl-6,000 µl, 100 µl-5,000 µl, 100 µl-4,000 µl, 100 µl-3,000 µl, 100 µl-2,000 µl, 100 µl-1,000 µl, 25 µl-10,000 µl, 25 µl-9,000 µl, 25 µl-8,000 µl, 25 µl-7,000 µl, 25 µl-6,000 µl, 25 µl-5,000 µl, 25 µl-4,000 µl, 25 µl-3,000 µl, 25 µl-2,000 µl, 25 µl-1,000 µl, 25 µl-900 µl, 25 µl-800 µl, 25 µl-700 µl, 25 µl-600 µl, 25 µl-500 µl, 25 µl-400 µl, 25 µl-300 µl, 25 µl-200 µl, 25 µl-100 µl, 25 µl-75 µl, and preferably 25 µl. The primary particle size of the API in suspension formulations also needs to be considered with regard to the droplet size delivered during dosing and any impact it may have on the dissolution of the particles once deposited in the nasal cavity.

pH/buffers suitable for the compositions of the invention for delivery to the nasal cavity of the upper respiratory tract include: the pH inside the nasal cavity can influence the rate and extent of absorption of ionizable drugs. The average baseline human nasal pH is reported to be around 6.3 and the pH of several commercially available nasal spray products are in the range of 3.5 to 7.0. In some embodiments of the invention, pH ranges for the nasal formulations can be from 4.5 to 6.5. In some embodiments, the compositions can have osmolality in the range: 100 m-1000 m, 100 m-900 m, 100 m-800 m, 100 m-700 m, 200 m-1000 m, 200 m-900 m, 200 m-800 m, 200 m-700 m, 300 m-3000 m, 300 m-900 m, 300 m-800 m, or preferably 300 m-700 m Osmol/K.

The compositions of the present invention may comprise one or more additional conventional components selected from thickeners, preservatives, emulsifiers, coloring agents, plasticizers and solvents.

Thickeners that may be used to adjust the viscosity of the composition, include those known to one skilled in the art, such as hydrophilic and hydroalcoholic gelling agents frequently used in the cosmetic and pharmaceutical industries. In some embodiments, thickeners include alginic acid, sodium alginate, cellulose polymers, carbomer polymers (carbopols), carbomer derivatives, cellulose derivatives (such as carboxymethyl cellulose, ethylcellulose, hydroxyethyl cellulose and hydroxypropyl cellulose), hydroxypropyl methyl cellulose (HPMC), polyvinyl alcohol, poloxamers (Pluronics®), polysaccharides (such as chitosan or the like), natural gums (such as acacia (arabic), tragacanth, xanthan and guar gums), gelatin, bentonite, bee wax, magnesium aluminum silicate (Veegum®) and the like, as well as mixtures thereof. Preferably, the hydrophilic or hydroalcoholic gelling agent comprises "CARBOPOL®" (B. F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). Other preferred gelling polymers include hydroxyethylcellulose, cellulose gum, MVE/MA decadiene crosspolymer, PVM/MA copolymer, or a combination thereof. In one preferred aspect, the viscosity of the compositions and formulations is adjusted by incorporation of a thickening agent, and preferably such that the quinine formulation increases residence time on the mucus membrane within ENT.

Preservatives may also be used in the compositions of the present invention and preferably comprise about 0.05% to 0.5% by weight of the composition. The use of preservatives assures that if the product is microbially contaminated, the formulation will prevent or diminish unwanted microorganism growth. Some preservatives useful in this invention include methylparaben, propylparaben, butylparaben, benzalkonium chloride, cetrimonium bromide (aka cetyltrimethylammonium bromide), cetylpyridinium chloride, benzethonium chloride, alkyltrimethylammonium bromide, methyl paraben, ethyl paraben, ethanol, phenethyl alcohol, benzyl alcohol, steryl alcohol, benzoic acid, sorbic acid, chloroacetamide, trichlorocarban, thimerosal, imidurea, bronopol, chlorhexidine, 4-chlorocresol, dichlorophene, hexachlorophene, chloroxylenol, 4-chloroxylenol, sodium benzoate, DMDM Hydantoin, 3-Iodo-2-Propylbutyl carbamate, potassium sorbate, chlorhexidine digluconate, or a combination thereof.

Suitable solvents include, but are not limited to, water or alcohols, such as ethanol, isopropanol, and glycols including propylene glycol, polyethylene glycol, polypropylene glycol, glycol ether, glycerol and polyoxyethylene alcohols. Polar solvents also include protic solvents, including but not limited to, water, aqueous saline solutions with one or more pharmaceutically acceptable salt(s), alcohols, glycols or a mixture there of. In one alternative embodiment, the water for use in the present formulations should meet or exceed the applicable regulatory requirements for use in drugs.

One or more emulsifying agents, wetting agents or suspending agents may be employed in the compositions. Such agents for use herein include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methylcellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-2lactylate; calcium stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerised fatty acids of soya bean oil; oxidatively polymerised soya bean oil; and pectin extract.

More preferably for nasal delivery of the composition described herein include a limited number of excipients that are listed in the US FDA inactive ingredient guide (IIG) for nasal products, which includes:

| Ingredients | IIG limit for nasal route (w/w) | Function |
|---|---|---|
| Alcohol, 200 proof | 2 | Co-solvent |
| Anhydrous dextrose | 0.5 | tonicity |
| Anhydrous trisodiumcitrate | 0.0006 | buffer |
| Benzyl alcohol | 0.0366 | preservative |
| Benzalkonium chloride | 0.119 | preservative |
| Butylated hydroxyanisole | 0.0002 | antioxidant |
| Cellulose microcrystalline stabilizer | 2 | Suspending agent, |
| Chlorobutanol | 0.5 | preservative |
| Carboxymethyl cellulose Na | 0.15 | Suspending agent |
| Edetate disodium | 0.5 | Chelator, antioxidant |
| Methylparaben | 0.7 | preservative |
| Oleic acid | 0.132 | Penetration enhancer |
| PEG400 | 20 | Surfactant, co-solvent |
| PEG3500 | 1.5 | surfactant |
| Phenylethyl alcohol agent | 0.254 | Preservative, masking |
| Polyoxyl 400 stearate | 15 | surfactant |
| Polysorbate 20 | 2.5 | surfactant |
| Polysorbate 80 | 10 | surfactant |
| Propylene glycol | 20 | Co-solvent |
| Propylparaben | 0.3 | Preservative |
| Sodium chloride | 1.9 | tonicity |
| Sodium hydroxide | 0.004 | pH adjustment |
| Sulfuric acid | 0.4 | pH adjustment |

Delivery and Administration

Any device can be used to administer the composition of present invention as a particulate on the mucosa of the ENT tract including, but not limited to, bulbs, inhalers, canisters, sprayers, nebulizers/atomizers, pipette, dropper, and masks. In one embodiment, the composition is packaged in conventional spray administration containers, provided that the container material is compatible with the formulation. In a preferred embodiment, the composition of the present invention is packaged in a container suitable for dispersing the composition as a mist directly into each nostril. For example, the container may be made of flexible plastic such that squeezing the container impels a mist out through a nozzle into the nasal cavity. Alternatively, a small pump may pump air into the container and cause the liquid spray to be emitted.

In an alternative embodiment, the composition of the present invention is packaged in a container pressurized with a gas which is inert to the user and to the ingredients of the composition. The gas may be dissolved under pressure in the container or may be generated by dissolution or reaction of a solid material which forms the gas as a product of dissolution or as a reaction product. Suitable inert gases which can be used include nitrogen, argon, and carbon dioxide.

Also, in other embodiments, the composition may be packaged in a pressurized container with a liquid propellant such as dichlorodifluoromethane, chlorotrifluoro ethylene, or some other conventional propellant.

In some embodiments, the composition of present invention is packaged in a metered dose spray pump, or metering atomizing pump, such that each actuation of the pump delivers a fixed volume of the formulation (i.e. per spray-unit) as particulate matter.

For administration in a dropwise manner, the composition of present invention may suitably be packaged in a container provided with a conventional dropper/closure device, comprising a pipette or the like, preferably also delivering a substantially fixed volume of the formulation.

Delivery Devices

One class of delivery devices suitable for delivery of the bitter taste receptor agonist are metered-dose inhalers. Metered dose inhalers offer multiple advantages such as portability, no external power source is required and formulation of a fixed-dose is delivered. The efficient aerosolized delivery of medication is possible through pressurized metered dose inhalers (pMDI). A pMDI is a pressurized system consisting of a mixture of propellants, flavouring agents, surfactants, preservatives and active drug composition. The drug delivery through the pMDIs takes place when the mixture is released from the delivery device through a metering valve and stem which fits into the design of an actuator boot. The smaller changes in the actuator design can affect the aerosol characteristics and output of pressurized metered dose inhaler. The newer pMDIs can be categorized as the coordination devices or breath-actuated. Breath-actuated pMDIs, such as the Easibreathe®, is a device that is designed to overcome the problem of poor coordination between the patient's breath and inhaler actuation. The Easibreathe® device works according to patient's breath rate and automatically adjust the trigger sensitivity for the activation of device. The pMDIs are breath-coordinated, devised to synchronize the inspiration rate along with discharge of the dose from inhaler. The reliability of the pMDIs can be ascertained through the coordinated inhalational flow rate between the drug actuation and patient variability. To reduce the droplet size after emission from the pMDIs, a smarter approach was proposed by Kelkar and Dalby that the addition of dissolved CO2 to Hydrofluoroalkane-134 and ethanol blend reduces the size of droplet. The advantage of spacer as a tube or extension device is that it is placed at the interface between the patient and the pMDI device. The use of VHCs (Valved holding chamber) such as AeroChamber Plus® Flow-Vu® allows inhalation and prevention of exhalation into the chamber consisting of one-way valve at the mouthpiece end. The advantage of VHC is that it does not require breath coordination as it enables the patient to breathe from a standing aerosol cloud. The phenomenon of electrostatic precipitation reduces the delivery of dose from the pMDIs. Inhalational drug delivery devices such as newer spacer devices and VHCs are responsible for minimizing the adherence of the emitted particles to the inner walls of the spacer as they are made up of anti-static polymers. The new generation spacers can indicate whether the patient is inhaling efficiently or is non-compliable regarding the therapy. Monodispersed aerosols with a very narrow range of particle sizes may target drug delivery to specific areas of the lung where it is most effective. However, as smaller particles are more easily absorbed into the pulmonary circulation via the alveoli, these formulations may be associated with a higher incidence of systemic side effects.

Another delivery device suitable for delivering the bitter taste receptor agonist are dry powder inhalers. The dry powder inhaler (DPI) delivers the medicaments to the mucosal layer of the ENT tract in form of the dry powder. Formulation of the dry powder inhaler delivers the aerosolized drug powder, where the formulation subjected to larger dispersion forces to deagglomerate into individual particles. The range of devices have been designed such as the Clickhaler, the Multihaler, and the Diskus which has the capability to feed the powder into a high-speed airflow that splits the aggregated particles, thus attaining the respirable particles. The devices Spinhaler and the Turbuhaler depend upon the mechanism of deagglomeration due to impaction between the particles and surfaces of the device. The design of dry powder inhalers is suffering from a limitation, that is the balance between flow rate and inhaler resistance in the device. In dry powder inhalers, a faster airflow is necessary for the increase in the particle deagglomeration and it is possible by the stronger impactions to achieve a higher fine particle fraction. While dry power inhalers have issues related to delivery to the lungs; the administration of the described compositions to mucosa of the ENT tract does not require the same level of penetration (to lungs) and thus avoids such issues.

The performance of a DPI system depends on performance of powder formulation and the inhaler device. The modern devices are being explored for different powder formulation (single or multiple dose powder inhalers) based on breath activated or power driven mechanism. The currently marketed passive devices depend on the inspiratory air flow of the patients for the powder dispersal into the individual particles. The DPI devices can be differentiated by the difference of resistance in air flow controlling the required inspiratory effort by the patient itself. In order to attain the maximum dose from the inhaler device, there should be appropriate generation of inspiratory flow rate which becomes difficult during the increase in the resistance of the device.

The dry powder inhalers can be classified accordingly with regards to some factors such as the mechanism of powder dispersion, number of loaded doses in the device, and patient's adherence and coordination with regard to powder aerosolized device. In single-dose DPIs, the dose is formulated inside the individual capsules. The mechanism for a single dose delivery is that the patient has to load the device with one capsule before each administration. The single-dose DPIs can further be classified as reusable or disposable device, whereas the multi-unit dose DPIs have the advantage that before administration of each dose it does not have to be reloaded as it utilizes the factory-metered and sealed doses packaged so that the device can hold multiple doses at the same time. The Rotahaler™ and the Spinhaler™, which are the single dose devices were also the first passive marketed dry powder inhalers. In the Rotahaler™, powder dose is loaded inside the capsule in the device.

The single use dry powder inhalers can be devised for oral drug delivery, as they are economic for use. MDIs offer reduced cost and convenient medication delivery in a compact and portable package. Capsule-based DPI technology is used for therapeutic application introduced in the middle of the last century with the introduction of the Aerohaler® for the delivery of antibiotics. The next device that was introduced at the end of the 1960s was the Spinhaler® as it was the first DPI containing a powder formulation of broncho active drugs in a gelatine capsule, which could be loaded into the device before its administration by the patient. Such devices can be modified to enable the device to deliver most or all of the dispersed powder to the mucosa of the ENT tract. In some embodiments, the available delivery options, mostly DPIs, consists of fine powder drug (particle size <5 μm) blended with larger carrier particles generally lactose. Presence of lactose helps to improve powder flow before the aerosolized delivery of the drug formulation. The powder formulations during inhalation or active forced dispersement can be deposited in the targeted regions of the nasal or mouth cavity. Further particles that are elongated have been found to attain a higher fine particle fractions released by the unstable interaction of the particles. The interaction between the drug and carrier particles is important to the performance of the formulation. The irregularity of the surface structures averts the particles from a closer interaction and with no difficulty in separation from each other upon aerodynamic stress. Change of surface characteristics of the capsule can be used for the modification of the powder retention to attain the optimal performance target within the formulation and the device. Breezhaler®: an example of recent capsule-based DPI. It is a single-dose DPI system with an improved Aerolizer technology consisting of design changes meant to improve device management and appearance. The Breezhaler is another device used for the delivery of drug from capsules. The design of the device has lower internal airflow resistance (0.15 cmH2O/L/min) as compared to the HandiHaler device (0.22 cmH2O/L/min) a capsule-based DPI system.

Turbuhaler is a device that contains up to 200 doses of drug stored in a reservoir and delivers the drug twice efficiently as pMDIs. The original formulation with micronised drug in Turbuhaler contains the pure drug only, although in recent formulations the active drug is blended with lactose particles of similar size to that of the drug particles. There are different types of nebulizers which delivers the formulation in the nano-scale are the most advanced ones. The development of the novel smarter drug carriers, is due to the progress in nanotechnology and advanced form of nebulization through liquid enable the delivery for these smart aerosolized particles. Nebulization devices are meant for the delivery of drug or formulation through the fine droplets. The optimization of inhalational particles for aerosol delivery should be done within the size range of 1-5 μm. The nebulizers such as jet, ultrasonic and nanodroplet nebulized aerosols generate particles between 1-5 μm in size. The nanocarrier delivery is achieved through the nebulized nanoparticles or suspensions. The nanocarrier delivery offers various advantages such as faster-onset, prolonged effect, greater regular dosing and efficiency equivalent at the lower level of doses. The new way to explore the nanodroplets is via the jet or ultrasonic nebulizers that can be designed to produce micro droplets and that can further generate the nanodroplets. The following are examples of DPI devices:

Spinhlaer (Aventis)—a dry powder contained within clear orange and white capsules called spincaps; Rotahaler (GlaxoSmithKline)—a breath actuated inhaler device releases medication from the Rotacap; Diskhaler (GlaxoSmithKline)—a dry-powder inhaler that holds small pouches (or blisters), each containing a dose of medication, on a disk; Diskus (GlaxoSmithKline)—used to treat sudden breathing problems from asthma or COPD; Turbuhaler (Astra Zeneca)—recommended with using the puffer and spacer available for emergencies; Handihaler (Boehringer-Ingelheim)—used to deliver the contents of Spiriva inhalation capsules containing the bronchodilator tiotropium; Tiotropium Inhalator (Boehringer-Ingelheim)—an easy to use device with fine finish, high strength, and dimensional accuracy; Cyclohaler (Pharmachemie)—a single dose system using gelatine capsules for drug formulation; Aerolizer (Novartis)—helps the muscles around the airways in your lungs stay relaxed to treat asthmatic condition; Pulvinal—used to treat chest illnesses and to avoid asthma symptoms brought on by exercise or other 'triggers; Easyhaler (Orion Pharma)—an environment friendly and efficient, easy to use for the treatment of respiratory illnesses such as asthma and chronic obstructive pulmonary disease (COPD); Clickhaler (Innovata Biomed/ML Labs Celltech)—effective at delivering the medication straight to the lungs where it is needed; Beclomethasone dipropionate Novolizer (ASTA Medica)—a multidose, refillable, delivers up to 200 metered doses of drug from a single cartridge; Twisthaler (Schering-Plough)—an inhalation device that is relatively independent of flow rates; Aerohaler (Boehringer-Ingelheim)—an easy to use inhaler which allows for breathe in the medicine from capsule, among others. Such devices can be further modified within the skills of an ordinary artisan to increase the particulate and/or decrease the airflow such that the particulate is delivered substantially or mostly to the ENT cavities of the nose and mouth.

In another example of delivery devices for delivery of bitter taste receptor agonists, and preferably quinine, and salts thereof, are nebulization and atomizer systems. During inspiration, the atmospheric air crosses the nebulizer for the aerosolized delivery while during exhalation the air inside the aerosol expels the aerosol to the outside of the atmosphere. Hence under atmospheric conditions there may be leakage of residual drug from the nebulizer. Jet nebuliser was the first technical operation developed for production of aerosol. It works on the mechanism of utilizing the gas flow from a compressor. The atomization of the formulation takes place through a small aperture in the nebulizer through which the gas passes. The atomized particles are air driven to a baffle and it consists of both small and large droplets. The impaction caused by the baffles effects the larger droplets and then forced onto the other side, meant to be recycled in the liquid form inside nebulizer. There may be significant loss of the aerosol particles during the exhalation due to leakage. There are further three types of jet nebulisers, which are defined according to their output during inhalation. Standard unvented nebulisers are used where there is a constant output during the patient's inhalation and exhalation phases.

Jet nebulizers—is a device preferred for aerosolized delivery, consists of following features such as—A. Additional inhaled air; B. Mouthpiece—it is meant for patient inhalation; C. Release of aerosol production through the orifice by passing the pressurized gas through it D. Baffle—the aerosol delivery takes place by passing through the baffles; E. Reservoir—it contains the suitable drug formulation; F. Pressurized air supply through the formulation.

Ultrasonic nebulisers are mostly preferred for aerosol therapy as they have a greater output capability than air jet nebulisers. The generation of aerosolized particles is through high frequency ultrasonic waves while the vibration required is within the range of (1.2-2.4 MHz) of a piezoelectric crystal. The vibration mechanism gets transferred to the liquid formulation which further produce a fountain of liquid-drug consisting of smaller and the larger droplets. The larger droplets are recovered into the liquid drug reservoir. The smaller droplets are stored inside the chamber of the nebulizer which is inhaled by the patient. In contrast with the jet nebulizer the residual mass which is confined in the nebulizer device, but the advantage of vibration mechanism overcomes the leakage as there is no gas source involved in the delivery of aerosol. There are two categories of ultrasonic nebulizers which are mostly used for inhalable therapy. Standard nebulisers are those where the drug is directly in contact with the piezo-electric transducer. This results into the increase in temperature of drug due to transducer heating. However piezoelectric transducer is difficult to sterilize.

Ultrasonic nebulisers with a water interface utilize water between the piezo-electric transducer and a distinct reservoir for the drug formulation. Water helps to reduce the drug from overheating and transducer. The ultrasonic nebulizer does not nebulize the liquids that are highly viscous or suspension or those having a higher surface tension. The aerosol is heated only when the residual mass is ~50% of the drug mass. Unlike compressed air nebulizers, ultrasonic nebulizers are expensive and bulky.

Mesh nebulisers can be used to deliver the liquid drug formulations as well as suspensions; however, in case of suspensions performance seems to be reduced with respect to the mass of inhaled aerosol and the output rate. Result of in vitro studies suggested that marketed mesh nebulisers reduce the nebulization time without affecting the efficiency of drug. The parameters that can influence the performance of marketed mesh nebulisers are the cleaning and disinfection. Static mesh nebulisers enable the delivery of liquid drug formulation inside the nebulizer, which is delivered by applying force. In 1980s Omron Healthcare (Bannockburn, IL, USA) introduced the first static mesh nebulizer. Mesh nebulizer offer an alternative means for sterilizing heat and moisture sensitive medical devices, that is not possible by autoclaving via submerging 0.10% solution of benzalkonium for 10-15 min. Vibrating mesh nebulisers utilize the vibration mechanism to deliver the liquid drug via the mesh. The annular piezo-element leads to mesh deformation which is possible due to its position, which is directly in contact with the mesh. Both the formulation and device are equally important for the successful use of the nebulisation system for the pulmonary targeting. The vibrating mesh nebulizers provide continuous nebulisation technology by generating aerosolized particles when it is most likely to reach the deep lung. Recent vibrating mesh nebulisers are portable devices capable to deliver precise doses with reduced wastage, convenience and energy efficiency along with high drug localization efficiency. The conical structure of the mesh with large cross sectional area makes the pumping and loading easy with the drug formulation. The mesh deformation affects the droplets through the holes, subsequently improving respiratory tract uptake of inhalants. There are three majors type of aerosol devices (MDI, DPI, and nebulizer) which are found to be safe and effective in certain clinical situations. Treatment with increased doses might need to increase the number of MDI puffs to achieve results equivalent to the larger nominal dose from a nebulizer. Design and lung deposition improvement of MDIs, DPIs, and nebulizers are exemplified by the new hydrofluoroalkane-propelled MDI formulation of beclomethasone, the metered-dose liquid-spray Respimat, and the DPI system of the Spiros. Another example is Aeroneb® Go, which is a vibrating mesh nebulizer that has horizontal mesh area consisting of 1000 holes vibrating at 100 kHz obtained by electrolysis. The release of droplets takes place from the holes of the mesh at a moderate velocity by impaction phenomenon at the base of the mesh nebulizer. The delivery of the aerosol particles takes place at low velocity. Some examples of nebulizer models capable of delivering the compositions of the invention to the ENT tract include:

| S. no. | Types of Marketed Product | Aerosol Device |
|---|---|---|
| 1 | Flovent Diskus | Metered dose inhalers |
| 2 | Breezhaler | Dry powder inhalers |
| 3 | AeroEclipseII BAN | Breath-actuated jet nebulizer |
| 4 | AKITA | Vibrating mesh |
| 5 | APIXNEB | Nebulizer |
| 6 | CompAIR | Jet Nebulizer |
| 7 | Omron NE-C801 | With virtual valve technology |
| 8 | I-neb AAD system | Vibrating mesh nebulizer |
| 9 | MicroAir NE-U22 | Vibrating mesh nebulizer |
| 10 | PARI LC Plus | Breath enhanced jet nebulizer |
| 11 | Side Stream Plus | Breath enhanced jet nebulizer |

One preferred atomizer is LMA® MAD NASAL™ Intranasal Mucosal Atomization Device (Teleflex, Morrisville, NC).

Another device capable of delivering the described liquid compositions are delivery devices from Silgan Holdings (Stamford, CT) that are capable of aerosolizing such liquid compositions. An additional array of devices capable of delivering the compositions of the invention are MDI, DPI, nasal pumps and other spray devices, and actuator-based delivery devices, such as devices from Aptar Pharma. For example, the delivery device can be a VP7 spray pump (Aptar Pharma), a pre-compression nasal spray pump, or the VP3 multi-dose pump spray device (Aptar Pharma). Pump delivery devices available from Nemera are also capable of delivering the presently described liquid compositions.

Additionally, exhalation delivery devices of Optinose (Yardley, PA) can be used to deliver the described compositions to the ENT cavities for application of the bitter taste receptor agonists to the mucosal layer therein. Preferably, regardless of the delivery device used, the formulations described herein are intranasally delivered to the nasal cavity where ciliated sinonasal cells reside; for an example the delivery device can apply the formulation to the posterior nasal cavity to coat the nasal turbinates. In some embodiments, the formulations herein are nebulized sprayed to the turbninates based on nasal modeling.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

ALI Viral Infection Model:

In vitro assessment of the effects of formulations of quinine solutions are completed in the Air Liquid Interface (ALI) model of cultured sinonasal epithelial cells. The earlier described studies utilizing the ALI model used bacteria which only reside on top of the cell and do not invade the cell. In this embodiment, the ALI model involves viruses, which invade into the cells and multiply using the host machinery of the cell. Also, using this model with the Middle East Respiratory Syndrome coronavirus (MERS-CoV), as an example, shows that infected cells in the ALI model also exhibited syncytial formation.

Sinonasal mucosal specimens were acquired from residual clinical material obtained during sinonasal Surgery, under an approved protocol and after obtaining Informed Consent. ALI cultures were established from human sinonasal epithelial cells (HSEC) enzymatically dissociated human tissue and grown to confluence in tissue culture flasks (75 cm) with proliferation medium consisting of DMEM/Ham's F-12 and bronchial epithelial basal medium (BEBM; Clonetics, Cambrex, East, N.J.) supplemented with 100 U/mL penicillin, 100 lug/mL streptomycin for 7 days. Cells were then trypsinized and seeded on porous polyester membranes (6-7×10" cells per membrane), in cell culture inserts (Transwell-clear, diameter 12 mm, 0.4 um pores; Corning, Acton, Mass.) coated with 100 uL of coating solution IBSA (0.1 mg/mL; Sigma-Aldrich), type I bovine collagen (30 g/mL; BD), fibronectin (10 ug/mL; BD) in LHC basal medium (Invitrogen) and left in a tissue culture laminar flow hood overnight. Five days later the culture medium was removed from the upper compartment and the epithelium was allowed to differentiate by using the differentiation medium consisting of 1:1 DMEM (Invitrogen, Grand Island, N.Y.) and BEBM (Clonetics, Cambrex, East Rutherford, N.J.) with the Clonetics complements for hEGF (0.5 ng/mL), epinephrine (5 g/mL). BPE (0.13 mg/mL). hydrocortisone (0.5 g/mL), insulin (5 g/mL), triiodothyronine (6.5 g/mL), and transferrin (0.5 g/mL), Supplemented with 100 UI/mL penicillin, 100 g/mL streptomycin, 0.1 nM retinoic acid (Sigma-Aldrich), and 10% FBS (Sigma-Ald rich) in the basal compartment. Human bronchial epithelial cells (Lonza, Walkersville, Md.) were similarly cultured as previously described. Microbiology swabs were processed by the clinical microbiology lab using both blood agar as well as MacConkey agar for isolation of gram-negative bacteria. Such cells and analytical methods are provided in US Patent Publication No 2015/0017099A1, which is incorporated by reference in its entirety.

Bitter taste receptor stimulation is capable of causing antimicrobial secretions by nasal epithelial cells (sinonasal ALI cultures). The apical surface of nasal ALI cultures can be washed with PBS (3×200 uL volume), followed by aspiration and addition of 30 uL of 50% PBS or 50% PBS containing denatonium, or one of the other bitter taste receptor agonists of the invention. After incubation at 37° C. for 30 minutes, the apical surface liquid (ASL, containing any secreted antimicrobials) can be removed and mixed with a virus, such as influenza or coronavirus. Low-salt conditions (50% PBS; 25% bacterial media) can be used because the antimicrobial activity of airway antimicrobials has been shown to have a strong salt-dependence. After incubation for 2 hours at 37° C., viral ASL mixtures can be plated with serial dilutions and incubated overnight. The ASL removed from cultures stimulated with denatonium will be confirmed for its antiviral activity.

Bitter taste receptor agonists of the present invention, including denatonium, absinthin or quinine (and salts thereof) can be used to stimulate antiviral activity in Sinonasal cell cultures to kill viruses, including for example influenza and coronavirus. The kill assay can apply ASL from cultures treated with 50% PBS alone (unstimulated), plus a bitter taste receptor agonist described herein. In some examples, the agonist is denatonium, absinthin, quinine (including salts thereof), and particularly can be 10 mM denatonium, and 300 uM absinthin.

Human ALI Infection with Influenza A:

Human Sinonasal ALIs were infected with H1N1 influenza A and the effect of quinine pretreatment on epithelial cell death and end point of viral load, as determined by qPCR, was assessed in a human ciliated sinonasal air-liquid-interface (ALI) model.

Figure 1B:
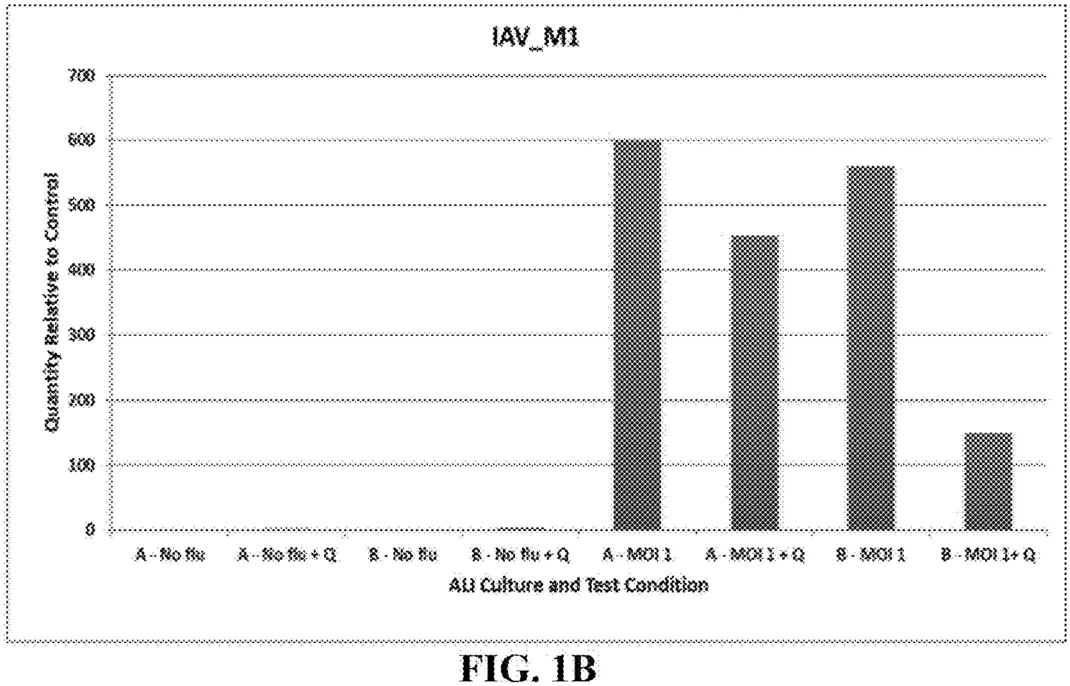

ALI derived from two separate patients (A and B) were established. ALI for subject B were more mature and had a higher density of cilia on the apical surface and thus were considered a priori as having greater responsiveness to quinine. Cells were infected with human H1N1 influenza A strain PR8 at either a multiplicity of infection (MOI) of 1 or 10. One hour post infection, the cells were stimulated with 0.1% quinine sulfate, dihydrate. The cells were maintained for 72 hrs while being fed and treated with quinine daily. Cells remained viable and visually healthy. Cells were collected at 72 hrs post-infection. Viral RNA was collected from the cell lysates. PCR of the viral NP, IAV-M1, and M1 genes was performed. As shown in FIG. 1 *a*) IAV_NP and 1b) IAV_M1, there was a marked relative reduction in transcripts for both the NP and IAV-M genes in the more mature subject B ALI culture and a lesser relative reduction for subject A cells at an MOI of 1 when treated with a 0.1% solution of quinine in 0.9% sodium chloride.

Experiments will test influenza A, parainfluenza, against human ciliated sinonasal epithelial cells in the ALI model from multiple human donors. Cultures will be assessed both from pre-treatment quinine followed by viral infection ½ hour later as well as post-infection treatment with cells infected for 1 hour and then treated an hour later with quinine that will be repeated daily for 3 days. ALI will be assessed for viability and viral RNA assessed daily via sampling from the apical fluid well to day three at which time the cells are harvested and stained for the presence of viral proteins. Cells will be infected at a multiplicity of infection of 1 and 5.

Figure 2A:
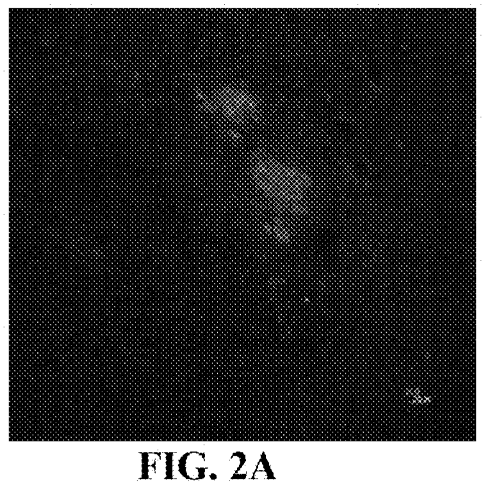
FIG. 2A depicts staining for the SARS-CoV-2 nucleocapsid protein (N), shown in red, as described in the Examples.
Figure 2B:
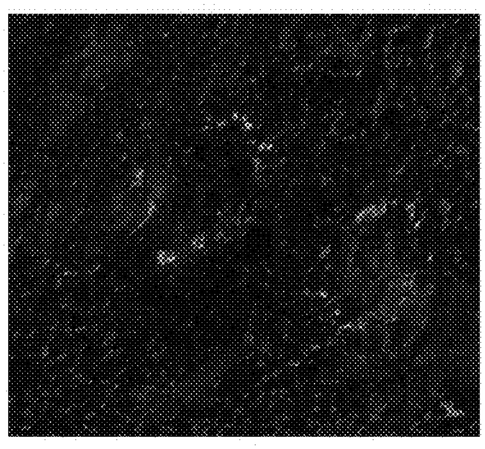
FIG. 2B depicts control staining for mucin (MUC5AC) or β-tubulin, shown in green, as described in the Examples.

Human ALI Infection with SARS-CoV-2:

Human Sinonasal ALIs were infected with the severe acute respiratory syndrome coronavirus type 2 (SARS-CoV-2). Mature ciliated ALI were infected for 1 hour with SARS-CoV-2 and the cells maintained for 72 hours. Staining for the SARS-CoV-2 nucleocapsid protein (N) is shown in red with control staining for mucin (MUC5AC) or β-tubulin shown in green in the two panels, respectively, in FIGS. 2A and 2B).

Human sinonasal epithelial cells were grown in tissue culture in an air-liquid interface (ALI) model. Cells were harvested from patients at the University of Pennsylvania as part of an ongoing protocol and approved study at the University. Material was maintained as deidentified, but with associated demographic and clinical data. Cultured cells will develop cilia on the air interface commensurate with clinical in-situ sinonasal epithelium. Such cells also produce mucus and evidence normal ciliary movement and ciliary beat frequency.

In another study, ALI of two patients were separated into individual wells and exposed to 10^4 of SARS-CoV-2 (UPenn/Philadelphia strain). After 1 hour, the cells were either treated with a solution of 1 mg/mL of quinine sulfate in 0.9% saline or left untreated. The cultured cells were then incubated with virus and quinine solution (as indicated) for 48 hrs after which the cells were harvested, fixed, and stained to detect the SARS-CoV-2 nucleocapsid protein in cells. Cells were also stained with 4'6-diamidino-2-phenylindole (DAPI) to detect nuclei of cells. The number of DAPI blue stained cells and infected (red stained) cells were then measured.

Figure 2C:
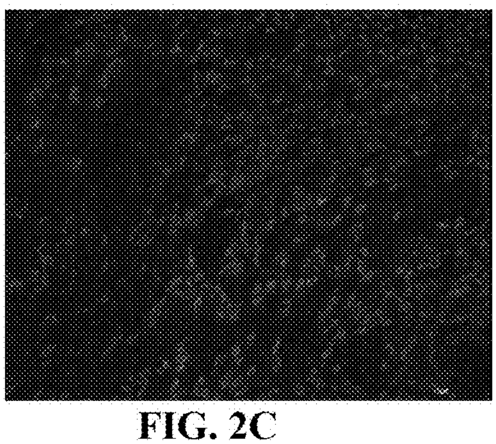
FIGS. 2C and 2D depict untreated (FIG. 2C) and quinine treated (FIG. 2D) cells in infection studies in an ALI model for a Hispanic male non-smoker of >80 years of age as described in the Examples.
Figure 2D:
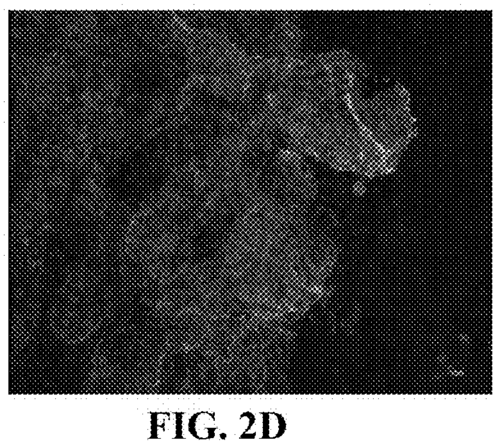

Infections studies in the ALI model are shown in FIGS. 2C and 2D for a Hispanic male non-smoker of >80 years of age. Untreated cells from this patient (shown in FIG. 2C) show a high frequency of SARS-CoV-2 infected cells (red stained cells), whereas quinine treated cells (shown in FIG. 2D) showed significantly fewer infected (red stained) cells.

Figure 2E:
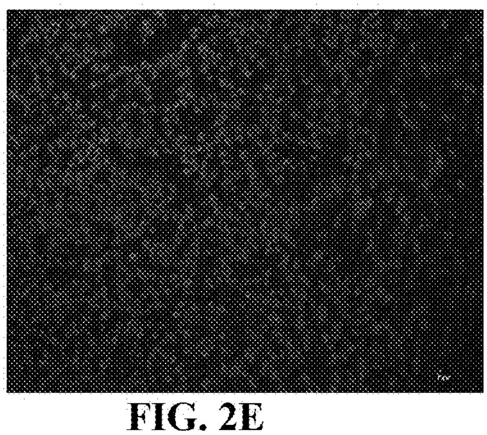
FIGS. 2E and 2F depict untreated (FIG. 2E) and quinine treated (FIG. 2F) cells in infection studies in an ALI model for a smoker male in their mid-fifties as described in the Examples.
Figure 2F:
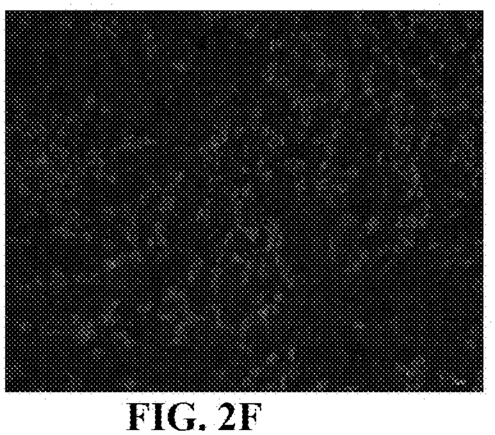

A second patient, a mid-50 year old male smoker, showed an even more dramatic decrease in SARS-CoV-2 infected cells. Untreated cells showed approximately 25% of cells infected (FIG. 2E) whereas treated cells were almost devoid of infection (FIG. 2F).

Infected cells were enumerated by quantitative fluorescence imaging. The average percent infected cells over two independent measurements from both patients are tabulated below.

| Patient # | Control (% infected) | Quinine Rx (% infected) | % reduction |
|---|---|---|---|
| >80 year old male | 25.08% | 2.32% | 90.7% |
| Mid 50's year old male | 27.74% | 11.10% | 60.0% |

Thus, these in vitro results demonstrate that quinine is effective in reducing SARS-CoV-2 infection in sinonasal ALI regardless of the age of the patient and regardless of smoking history. Moreover, this effect was despite the virus remaining in the culture medium for the full period of cellular incubation, an experimental condition that would favor viral growth.

Figures 3A, 3B, 3C:
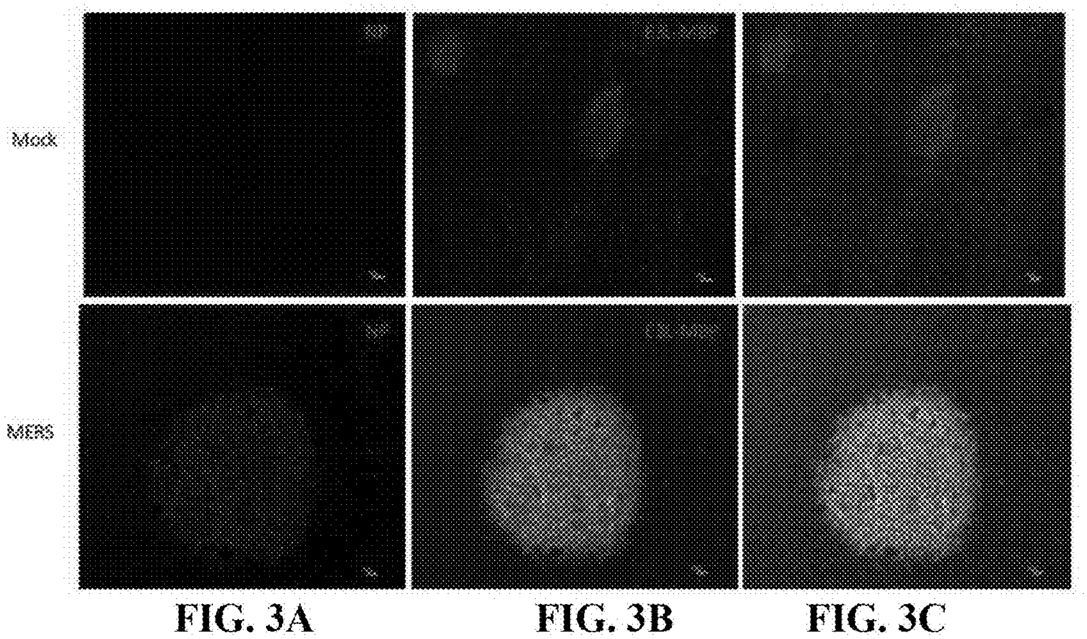
FIGS. 3A, 3B and 3C depict human sinonasal ALIs infected with MERS-CoV with staining for the MERS-CoV nucleocapsid protein (N) shown in red and with control staining for mucin (MUC5AC) or β-tubulin shown in green, as described in the Examples.

Human ALI Infection with MERS-CoV-2:

Human Sinonasal ALIs were infected with the Middle East Respiratory syndrome coronavirus (MERS-CoV). Mature ciliated ALI were infected for 1 hour with SARS-CoV-2 and the cells maintained for 72 hours. Staining for the MERS-CoV nucleocapsid protein (N) is shown with control staining for mucin (MUC5AC) or (β-tubulin shown in FIGS. 3A through 3C, respectively.

The effect of quinine pretreatment or post-treatment to prevent MERS-CoV infection to prevent epithelial cell death will be assessed in ALI over a 3-day infection period. In one experiment, cells will be pre-treated with quinine at 1 mg/ml for 1 hour, washed with PBS, and then infected at an MOI of 1 for 1 hr. Cells will be incubated for 3 days with virus sampled in the apical fluid by qPCR on each day and cells harvested on day 3 to detect intracellular virus as above. In another experiment, cells will be infected with MERS-CoV for 1 hr, washed with PBS, and then treated with quinine for ½ hr and again daily at 1 mg/ml. Cells will be incubated for three days. Viral replication will be determined by qPCR from the apical fluid and on day 3 the cells will be harvested and virus detected in the cells by immunohistochemistry as above.

Human ALI Infection with SARS-CoV-2:

Human Sinonasal ALIs were infected with the SARS-CoV2 (COVID-19). Mature ciliated ALI were infected for 1 hour with SARS-CoV-2 and the cells maintained for 72 hours. Staining for the SARS-CoV2 nucleocapsid protein (N) is shown in FIGS. 4A through 4D.

As suggested by the green staining, the assay shows the first successful infection of SARS-CoV2 in human sinonasal cells.

Quinine Protection in Ferret Challenge Model of SARS-CoV-2:

Ferrets are one of only a few animals that are susceptible to SARS-CoV-2 and develop illness. Nasal instillation of a 0.1% (1 mg/mL) solution of quinine sulfate dihydrate in 0.9% saline (normal saline, NS) induces release of nitric oxide (NO) and also protects ferrets against SARS-CoV-2 infection. Female ferrets, 6-8 weeks of age, underwent assessment of NO production after stimulation of nasal epithelial cells following nasal instillation of a 1 mg/mL solution of quinine sulfate dihydrate in 0.9% sodium chloride. Twelve ferrets were divided into four groups.

Following induction of anesthesia with isoflurane, the nares were flushed with 1 mL of saline. After the saline wash, 200 μL of either quinine or phosphate buffered saline (PBS) was instilled with nine animals receiving quinine and three PBS. Following treatment, a nasal wash was performed at 5 min for the animals that were treated with PBS and the effluent collected for NO measurement. The nine quinine treated animals were divided into three groups of three animals. Nasal washes were performed at 5 min for one group, at 10 min for a second group, and at 15 min for the third group post-treatment with the effluent collected for NO measurement. NO assessments were blind to treatment. The effluents were immediately frozen and then assayed at the University of Pennsylvania for NO levels. Whereas quantitative assessment of NO in PBS treated animals was 5.58 ng/mL, NO in the quinine treated animals was 6.64 ng/mL at 5 min, 6.42 at 10 min, and 6.52 at 15 min demonstrating that NO production was increased over baseline in all animals and remained persistently elevated for at least 15 min post-treatment.

After a 3-day washout period, the same 12 ferrets were then challenged with SARS-CoV-2 (strain designation as SARS-CoV-2/Canada/ON/VIDO-01/2020/Vero'76/p.2). Two of the four groups of three ferrets were treated with 200 μL of quinine into one nostril and the other two groups were treated with PBS. Five minutes post-treatment, the animals were challenged with 25 μL per nostril of SARS-CoV-2. For two groups (PBS and quinine treated), the challenge dose was 10*4 TCID50 while two groups were challenged with a dose of 10*5 TCID50. Each animal was treated a second time 24 hrs post-challenge with either PBS or quinine per the original treatment assignment. Nasal washes were collected on days 1 (pre-treatment) and again 3 post challenge. Animals were sacrificed on day 3 and turbinate tissue collected for quantitative measurement of viral load by rtPCR.

Nasal washes showed a decrease in viral load for treated animals at both days post-infection with the most dramatic differences observed on day 3 post-challenge. Viral load measurements are shown in the Table, below. Moreover, of the 6 animals treated with quinine and challenged with either a low or high challenge viral challenge with SARS-CoV-2, only 1 of 6 (16.7%) of animals had detectable virus on Day 1 post-challenge vs 2 of 6 (33%) of controls and 50% vs 67% on day 3, respectively.

| Treatment | Day 1 | Day 1 | Day 3 | Day 3 |
|---|---|---|---|---|
| Challenge dose> | 10^4 | 10^5 | 10^4 | 10^5 |
| Quinine (0.1% in NS) | 1 | 5 | 19 | 5 |
| PBS | 31 | 42 | 594 | 84,350 |

Measurement of virus in turbinate tissue taken at necropsy similarly demonstrated that treated animals had markedly lower viral mean viral loads regardless of the challenge dose (see Table, below).

| Treatment | Day 3 | Day 3 |
|---|---|---|
| Challenge dose> | 10^4 | 10^5 |
| Quinine (0.1% in NS) | 1 | 5,000 |
| PBS | 440,000 | 220,000 |

These data demonstrate that intranasal quinine instillation as a 1 mg/mL solution in 0.9% saline effectively reduced SARS-CoV-2 infection in nasal turbinates of ferrets. Of note, is that animals were pre-treated 5 min before viral challenge and given only a single post-challenge treatment 24 hrs later. Since any residual virus would be expected to grow quickly post-treatment in the absence of an anti-viral effect, it shows significant reduction of virus even with a single treatment and the potential value of this treatment both as a prophylaxis and as a therapeutic to reduce nasal colonization and infection.

Human Clinical Trials

The use of quinine sulfate dihydrate is also being tested in a Phase II clinical trial as prophylaxis against incident SARS-CoV-2 infection. This clinical trial (NCT 04408183) is a randomized, placebo-controlled, double-blind study of a formulated solution of quinine sulfate (1 mg/mL, pH 6) administered via nasal atomizer. Study participants are randomized 2:1 to either quinine or placebo treatment, respectively, and self-administer study drug for a total of 28 days. Study drug has been well tolerated with no serious adverse events to date. Nasopharyngeal swabs to determine the presence of SARS-CoV-2 by PCR will be collected at baseline and again at 2, 4 and 6 weeks.

What is claimed is:

1. A method of treating a viral infection in a subject having an upper respiratory infection, comprising:

dispersing as particulate a formulation of a bitter taste receptor agonist, wherein the bitter taste receptor agonist is selected from the group consisting of: denatonium, phenylthiocarbamide (PTC), a homoserine lactone, sodium thiocyanate (NaSCN), 6-n-propylthio uracil (PROP or PTU), parthenolide, amarogentin, antidesma, antidesma extract, colchicine, dapsone, salicin, quinine, and quinine salts;

applying the dispersed formulation onto the mucosal surface of an upper respiratory cavity of the subject; and generating nitric oxide (NO) production or stimulating antimicrobial peptide production, or both, through the stimulation of bitter taste receptors;

wherein the viral infection is an infection resulting from a virus selected from the group consisting of: SARS; SARS-CoV-2; MERS-CoV; SARS-CoV; adenovirus; human metapneumovirus; respiratory syncytial virus; and non-pathogenic coronaviruses.

2. The method of claim 1, wherein the bitter taste receptor agonist is selected from the group consisting of: quinine, and quinine salts.

3. The method of claim 2, wherein the quinine salt is quinine sulfate dihydrate.

4. The method of claim 3, wherein the quinine is formulated in sterile saline at a concentration of between 0.5 mg/ml and 1 mg/ml.

5. The method of claim 1, wherein the viral infection is an infection resulting from a virus selected from the group consisting of: SARS; SARS-CoV-2; MERS-CoV; SARS-CoV and non-pathogenic coronaviruses.

6. The method of claim 1, wherein the dispersing and applying steps are repeated three times per day using a nasal delivery device.

7. The method of claim 6, wherein the nasal delivery device is a metered dose inhaler, dry powder inhaler, dropper, nebulizer, atomizer, or lavage.

8. The method of claim 6, wherein the repeating of atomizing and applying steps three times per day is continued for four weeks.

9. The method of claim 1, wherein the viral infection is an infection resulting from a virus selected from the group consisting of: SARS; SARS-CoV-2; MERS-CoV; and SARS-CoV.

10. The method of claim 1, wherein the viral infection is an infection resulting from SARS-CoV-2 virus.

11. A method of treating a viral infection in a subject having an upper respiratory infection, comprising:

dispersing as particulate a formulation of a bitter taste receptor agonist at a concentration of between 0.5 mg/ml and 1 mg/ml;

applying the dispersed formulation onto the mucosal surface of an upper respiratory cavity of the subject; and generating nitric oxide (NO) production or stimulating antimicrobial peptide production, or both, through the stimulation of bitter taste receptors;

wherein the viral infection is an infection resulting from a virus selected from the group consisting of: SARS; SARS-CoV-2; MERS-CoV; SARS-CoV; adenovirus; human metapneumovirus; respiratory syncytial virus; and non-pathogenic coronaviruses.

12. The method of claim 11, wherein the viral infection is an infection resulting from a virus selected from the group consisting of: SARS; SARS-CoV-2; MERS-CoV; and SARS-CoV.

13. The method of claim 11, wherein the viral infection is an infection resulting from SARS-CoV-2 virus.

* * * * *